US00PP33791P2

(12) United States Plant Patent
van der Voort

(10) Patent No.: US PP33,791 P2
(45) Date of Patent: Dec. 28, 2021

(54) ***VERBENA* PLANT NAMED 'VERBDF'**

(50) Latin Name: *Verbena bonariensis*
Varietal Denomination: VERBDF

(71) Applicant: Rob van der Voort, Hazerswoude-Dorp (NL)

(72) Inventor: Rob van der Voort, Hazerswoude-Dorp (NL)

(73) Assignee: VAN HEMERT & Co. B.V., Hazerswoude-Dorp (NL)

( * ) Notice: Subject to any disclaimer, the term of this patent is extended or adjusted under 35 U.S.C. 154(b) by 0 days.

(21) Appl. No.: 17/147,228

(22) Filed: Jan. 12, 2021

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./263.1, 308
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Verbena* plant named 'VERBDF', characterized by its relatively compact, upright to outwardly spreading plant habit; moderately vigorous to vigorous growth habit; freely branching habit; narrowly oblanceolate leaves; freely flowering habit; purple-colored flowers that are night fragrant; and good garden performance.

1 Drawing Sheet

Botanical designation: *Verbena bonariensis.*
Cultivar denomination: 'VERBDF'.

STATEMENT REGARDING PRIOR DISCLOSURES BY THE INVENTOR/APPLICANT & ASSIGNEE

An European Community Plant Breeder's Rights application for the instant plant was filed by the Assignee, Van Hemert & Co B.V. of Hazerswoude-Dorp, The Netherlands on Oct. 8, 2019, application number 2019/2566. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Verbena* plant, botanically known as *Verbena bonariensis* and hereinafter referred to by the name 'VERBDF'.

The new *Verbena* plant is a product of a planned breeding program conducted by the Inventor in Hazerswoude, The Netherlands. The objective of the breeding program is to create new compact and uniform *Verbena* plants with numerous attractive flowers.

The new *Verbena* plant originated from a cross-pollination made by the Inventor in August, 2012 in Hazerswoude, The Netherlands of a proprietary selection of *Verbena bonariensis* identified as code designation BR, not patented, as the female, or seed, parent with a proprietary selection of *Verbena bonariensis* identified as code designation B1, not patented, as the male, or pollen, parent. The new *Verbena* plant was discovered and selected by the Inventor as a single flowering plant within the progeny of the stated cross-pollination in a controlled greenhouse environment in Hazerswoude, The Netherlands in July, 2013.

Asexual reproduction of the new *Verbena* plant by terminal vegetative cuttings in a controlled greenhouse environment in Hazerswoude, The Netherlands since September, 2013 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'VERBDF'. These characteristics in combination distinguish 'VERBDF' as a new and distinct *Verbena* plant:

1. Relatively compact, upright to outwardly spreading plant habit.
2. Moderately vigorous to vigorous growth habit.
3. Freely branching habit.
4. Narrowly oblanceolate leaves.
5. Freely flowering habit.
6. Purple-colored flowers that are night fragrant.
7. Good garden performance.

Plants of the new *Verbena* differ primarily from plants of the female parent selection in flower color as plants of the new *Verbena* have darker purple-colored flowers than plants of the female parent selection. In addition, plants of the new *Verbena* are more compact than plants of the female parent selection.

Plants of the new *Verbena* differ primarily from plants of the male parent selection in branching habit as plants of the new *Verbena* are more freely branching than plants of the male parent selection. In addition, plants of the new *Verbena* are taller than plants of the male parent selection.

Plants of the new *Verbena* can be compared to plants of the *Verbena bonariensis* 'Buenos Aires', not patented. In side-by-side comparisons, plants of the new *Verbena* differ primarily from plants of 'Buenos Aires' in the following characteristics:

1. Plants of the new *Verbena* are more compact than plants of 'Buenos Aires'.
2. Flowers of plants of the new *Verbena* are somewhat more blue purple in color than flowers of plants of 'Buenos Aires'.
3. Flowers of plants of the new *Verbena* are night fragrant whereas flowers of plants of 'Buenos Aires' are not fragrant.

BRIEF DESCRIPTION OF THE PHOTOGRAPH

The accompanying colored photograph illustrates the overall appearance of the new *Verbena* plant showing the colors as true as it is reasonably possible to obtain in colored reproductions of this type. Colors in the photograph may differ slightly from the color values cited in the detailed botanical description which accurately describe the colors of the new *Verbena* plant.

The photograph is a side perspective view of typical flower plants of 'VERBDF' grown in an outdoor nursery.

DETAILED BOTANICAL DESCRIPTION

The aforementioned photograph and following observations, measurements and values describe plants grown ground bed and in 17-cm containers during the summer and autumn in an outdoor nursery in Hazerswoude, The Netherlands and under cultural practices typical of commercial *Verbena* production. During the production of the plants, day temperatures ranged from 16° C. to 24° C. and night temperatures ranged from 12° C. to 16° C. Plants were five months old when the photograph and description were taken. In the description, color references are made to The Royal Horticultural Society Colour Chart, 2015 Edition, except where general terms of ordinary dictionary significance are used.

Botanical classification: *Verbena bonariensis* 'VERBDF'.

Parentage:

*Female, or seed, parent*.—Proprietary selection of *Verbena bonariensis* identified as code designation BR, not patented.

*Male, or pollen, parent*.—Proprietary selection of *Verbena bonariensis* identified as code designation B1, not patented.

Propagation:

*Type*.—Terminal vegetative cuttings.

*Time to initiate roots, summer*.—About ten days at temperatures about 22° C.

*Time to initiate roots, winter*.—About 18 days at temperatures about 22° C.

*Time to produce a rooted young plant, summer*.—About 30 days at temperatures about 18° C. to 20° C.

*Time to produce a rooted young plant, winter*.—About 40 days at temperatures about 18° C. to 20° C.

*Root description*.—Medium in thickness, fibrous; typically light brown to cream in color, actual color of the roots is dependent on substrate composition, water quality, fertilizers, substrate temperature and age of roots.

*Rooting habit*.—Not freely branching; medium density.

Plant description:

*Plant habit*.—Relatively compact, upright to outwardly spreading plant habit; freely branching habit with about six primary lateral branches each with about 14 secondary lateral branches; dense and bushy plant habit; moderately vigorous to vigorous growth habit; moderate to rapid growth rate.

*Plant height, soil level to top of foliar plane*.—About 69.5 cm.

*Plant height, soil level to top of floral plane*.—About 97 cm.

*Plant diameter*.—About 63.5 cm.

Lateral branch description:

*Length*.—About 56.5 cm.

*Diameter*.—About 2 mm.

*Internode length*.—About 9.8 cm.

*Strength*.—Strong.

*Aspect*.—Upright to about 40° from vertical.

*Texture and luster*.—Densely pubescent; moderately glossy.

*Color, developing*.—Close to 146B.

*Color, developed*.—Close to between 143B and 144A.

Leaf description:

*Arrangement*.—Opposite, simple; sessile.

*Length*.—About 6.9 cm.

*Width*.—About 9 mm.

*Shape*.—Narrowly oblanceolate.

*Apex*.—Acute.

*Base*.—Decurrent.

*Margin*.—Coarsely serrate.

*Texture and luster, upper surface*.—Densely pubescent, moderately rugose; moderately glossy.

*Texture and luster, lower surface*.—Densely pubescent, slightly rugose; matte.

*Venation pattern*.—Pinnate.

*Color*.—Developing leaves, upper surface: Close to 137B. Developing leaves, lower surface: Close to 137C. Fully expanded leaves, upper surface: Close to NN137A; venation, close to 146B. Fully expanded leaves, lower surface: Close to between 137B and 147B; venation, close to 147C.

Flower description:

*Flower arrangement and habit*.—Salverform flowers arranged in hemispherical terminal and axillary compound cymes; numerous cymes per plant; flowers face upward to slightly outwardly depending on position in the cyme; freely flowering habit with about 120 flowers developing per inflorescence and about 10,000 flowers and flower buds developing per plant.

*Fragrance*.—Faintly night fragrant; sweet and pleasant.

*Natural flowering season*.—Plants flower continuously from the spring through the fall in The Netherlands; plants begin flowering about twelve weeks after planting.

*Flower longevity*.—Individual flowers last about one week on the plant; flowers persistent.

*Inflorescence height*.—About 3.3 cm.

*Inflorescence diameter*.—About 2.9 cm.

*Flower buds*.—Length: About 4 mm. Diameter: About 0.8 mm. Shape: Narrowly oblanceolate. Texture and luster Immature sepals, sparsely pubescent and matte; immature petals, smooth, glabrous and matte. Color: Immature sepals, close to 60A; immature petals, close to 90B; proximally, close to N144D.

*Flowers*.—Appearance: Salverform, five-parted fused corolla. Diameter: About 4.5 mm. Depth: About 8 mm.. Throat diameter: About 1 mm Tube length: About 7 mm. Tube diameter: About 0.9 mm.

*Corolla*.—Arrangement: Single whorl of five fused petals; 78% of petal length is fused. Petal length: About 7 mm. Petal lobe width: About 1.5 mm. Petal lobe shape: Orbicular. Petal lobe apex: Emarginate. Petal margin: Entire, not undulate. Petal texture and luster, upper surface: Smooth, glabrous; slightly velvety; matte. Petal texture and luster, lower surface: Smooth, glabrous; matte. Throat texture and luster: Smooth, glabrous; matte. Tube texture and luster: Moderately pubescent; matte. Color: Petal lobe, when opening, upper and lower surfaces: Close to N87B. Petal lobe, fully opened, upper and lower surfaces: Close to N87B; venation, close to N87B; color becoming closer to 90C with development. Throat: Close to N88D; venation, close to N88D. Tube: Close to 71A; venation, close to 71A.

*Calyx*.—Arrangement: Star-shaped calyx with five fused sepals; 90% of the sepal length is fused. Length: About 4 mm. Diameter: About 1 mm. Sepal length: About 4 mm. Sepal width: About 0.5 mm. Sepal shape: Narrowly oblanceolate. Sepal apex: Acute. Sepal margin: Entire. Sepal texture and luster, upper surface: Smooth, glabrous; slightly glossy. Sepal texture and luster, lower surface: Moderately pubescent; slightly glossy. Sepal color, when developing, upper and lower surfaces: Distally, close to 60A and proximally, close to N144D. Sepal color, fully developed, upper and lower surfaces: Distally, close to N77B and proximally, close to 144C to 144D.

*Peduncles*.—Length: About 1.4 cm. Diameter: About 1.25 mm. Strength: Strong. Aspect: Upright to about 45° from vertical. Texture and luster: Densely pubescent; matte. Color: Close to 146A; distally, close to 183D.

*Pedicels*.—Length: About 0.3 mm. Diameter: About 0.4 mm. Strength: Moderately strong. Aspect: Upright to about 45° vertical. Texture and luster: Moderately pubescent; matte. Color: Close to 144B.

*Reproductive organs*.—Stamens: Quantity and arrangement: About four per flower. Filament length: About 0.3 mm. Filament color: Close to N155A. Anther size: About 0.2 mm by 0.5 mm. Anther shape: Narrowly oblong. Anther color: Close to 151C. Pollen amount: Scarce. Pollen color: Close to 11D. Pistils: Quantity: One per flower. Pistil length: About 2 mm. Style length: About 1.7 mm. Style color: Close to 146D. Stigma diameter: About 0.3 mm. Stigma shape: Club-shaped. Stigma color: Close to 146A. Ovary color: Close to 146D. Seeds and fruits: To date, seeds and fruit development has not been observed on plants of the new *Verbena*.

Garden performance: Plants of the new *Verbena* have been observed to have good garden performance, to tolerate temperatures ranging from about −7° C. to about 35° C. and to be suitable for USDA Hardiness Zones 8 through 11.

Pathogen & pest resistance: To date, plants of the new *Verbena* have not been observed to be resistant to pathogens and pests common to *Verbena* plants.

It is claimed:

1. A new and distinct *Verbena* plant named 'VERBDF' as illustrated and described.

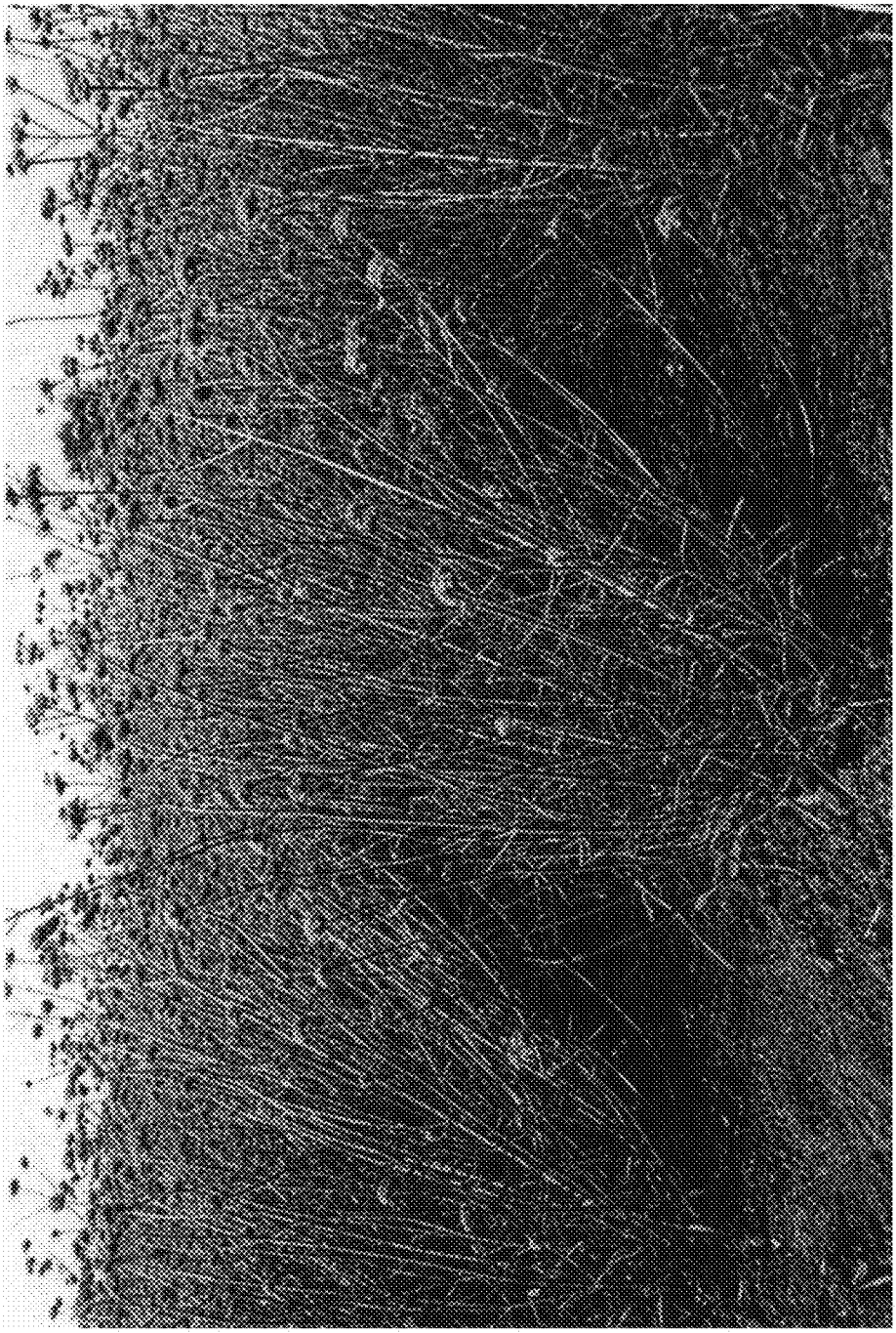

* * * * *